United States Patent [19]

Modrovich et al.

[11] Patent Number: 4,652,524
[45] Date of Patent: Mar. 24, 1987

[54] SOLUBLE STABILIZED ENZYMES

[75] Inventors: Ivan E. Modrovich, 1043 Mesa Dr., Camarillo, Calif. 93010; Paul F. Wegfahrt, Jr.; Wanda A. Gaussiran, both of Camarillo, all of Calif.

[73] Assignee: Ivan E. Modrovich, Camarillo, Calif.

[21] Appl. No.: 193,116

[22] Filed: Oct. 2, 1980

[51] Int. Cl.$^4$ .......................... C12N 9/96; C12Q 1/52; C12Q 1/50; C12Q 1/42; C12Q 1/32

[52] U.S. Cl. ...................................... 435/188; 435/16; 435/17; 435/21; 435/26

[58] Field of Search .................. 424/94; 435/4, 11–28, 435/174, 180, 181, 188, 182

[56] References Cited

U.S. PATENT DOCUMENTS 3,860,484  1/1975  O'Malley ............................. 435/188
4,017,364  4/1977  Leemputten ........................ 435/180
4,226,938  10/1980  Yoshida et al. ..................... 435/182
4,250,254  2/1981  Modrovich ......................... 435/188

FOREIGN PATENT DOCUMENTS 1286095  8/1972  United Kingdom ................ 435/188

Primary Examiner—Esther M. Kepplinger
Attorney, Agent, or Firm—Christie, Parker & Hale

[57] ABSTRACT

A method is disclosed for preparing a soluble stable enzyme. The method comprises the steps of reacting in a liquid media an enzyme with a polymer having pendant groups capable of covalently bonding with pendant groups on the enzyme. The enzyme and polymer are mixed with at least one composition which affects the activity of the enzyme. Such a composition can be selected from the enzyme substrate, product of the enzyme substrate reaction, an activator for the enzyme and/or inhibitor for the enzyme. In addition, a composition can be added which can also competitively react with the available pendant groups of the polymer.

21 Claims, 5 Drawing Figures

U.S. Patent    Mar. 24, 1987    4,652,524
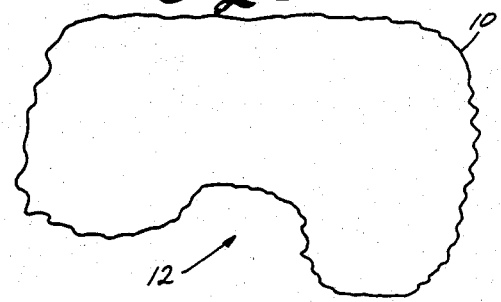
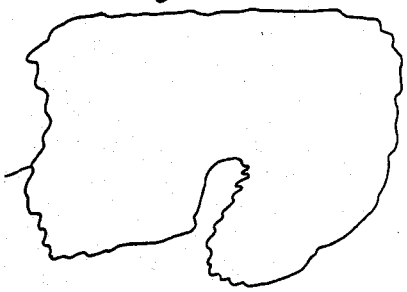
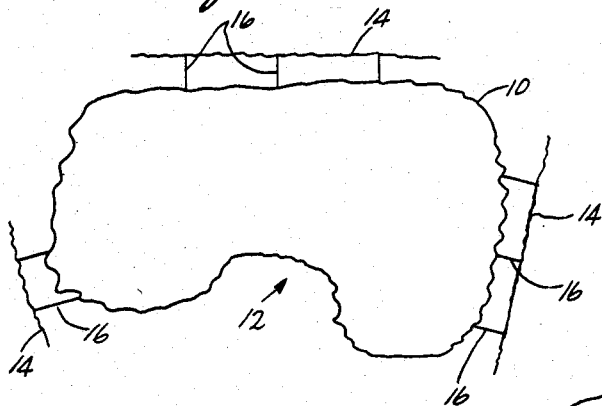
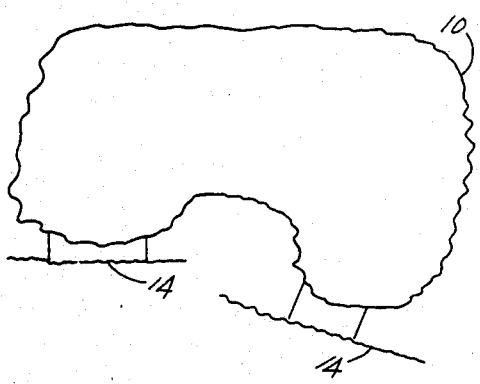
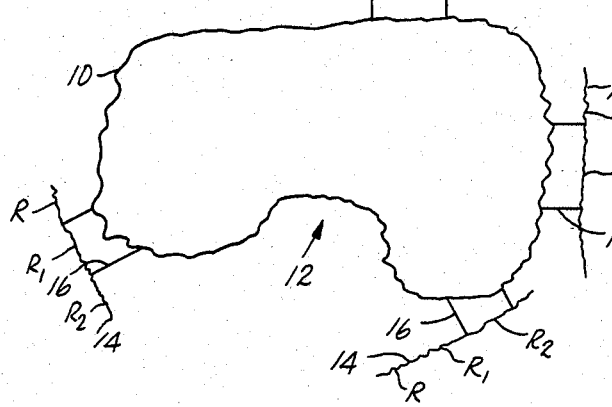

SOLUBLE STABILIZED ENZYMES

BACKGROUND OF THE INVENTION

The present invention relates to the stabilization of labile enzymes in solutions. In a particular aspect, the present invention relates to soluble stabilized enzymes which can be useful in clinical diagnostic assays.

Enzymes are large molecular weight complex protein molecules, usually of unknown chemical structure. They are presently classified by their catalytic activity and extreme substrate specificity. Enzymes may be redefined as biological catalysts, capable of catalyzing a reaction of a single substrate or a reaction of a similar group of substrates.

Stability of enzymic solutions used in diagnostic assays is important in providing methods of analysis which exhibit precision and uniformity among separate determinations when conducted over a period of elapsed time. Instability of enzymic solutions, in addition to not providing reproducibility of assays, can also add to the ever increasing cost of medical services because the unstable enzymic solutions need to be discarded and fresh solutions formulated.

It has recently been estimated that about 25 percent of all in vitro diagnostic tests conducted annually in the United States are unreliable. Unreliable tests can result in unnecessary medical treatment, the withholding of necessary treatment and lost income. Because of their high specificity, the use of enzyme determinations has significantly increased during the last few years and indications are that this trend will continue. However, rigorous quality control measures are required to assure the accuracy and consistency of results. This requirement derives from the fact that the exact nature of enzymes, as well as mechanisms of their reactions remains unknown for the most part.

At present, the greatest limitation in the diagnostic reagent manufacture, by far, lies in the unstable characteristics of the enzymic solutions. Current diagnostic methodologies require the use of labile ingredients. Due to the labile nature of the enzymes, rigorous quality control is required over the production of such enzymic solutions, in the reconstituting dry media preparations and formulation of such enzymic solutions. Such quality control is costly. Moreover, if such control in any step in the process is not maintained within a high degree of precision, the quality of the final product can be reduced materially leading to the decreased precision in assay results.

The present commercial state of the art used for stabilizing the reactive ability of enzymes is by locking them into a solid matrix, either by freeze drying, dry blending such as used for tableting dry powders primarily in the pharmaceutical, diagnostic and related industries, and immobilization by locking the chemical structure of the enzyme into a solid matrix. Contrary to the sophistication these terms imply, these approaches are neither practical nor desirable and are also expensive. The manufacturer is forced to remove the water and supply a partial product, thus relinquishing part of the quality control cycle in the dilution and use of the final product. Laboratories are forced to pay the high cost of packaging, reagent waste, freeze drying and dry blending. Usefulness of the product is further limited by packaging modes and sizes.

Furthermore, good product uniformity is difficult to achieve, especially in the laboratories where the products are to be utilized in diagnostic assay. Generally, the reconstituted freeze-dried solutions have a relatively short stability such as about 24 hours to 5 days at room temperature conditions. Their use is then limited by such a short shelf-life.

The present invention is uniquely designed so that the enzyme solutions, although containing labile ingredients in a liquid regent, are effectively "stabilized" thereby controlling the activity of the labile ingredients in the liquid solution. This method of providing stability insures long-term stability in a liquid media. Moreover, close tolerance control can be achieved in the manufacturing of a high quality product which eliminates the inconvenience of the rigid package size, the high cost of packaging and freeze drying, and reagent waste.

In the clinical diagnostic field the commercial application of enzymic analysis is represented by, but not limited to, the diagnostic reagents used to determine and quantitate the following constituents in biological fluids;

1. glumatic-oxalacetic transaminase (SGOT);
2. glutamic-pyruvic transaminase (SGPT);
3. lactic dehydrogenase (LDH);
4. creatine phosphokinase (CPK);
5. α-hydroxybuteric dehydrogenase (α-HBD);
6. glucose (via hexokinase-G-6-PDH or glucose dehydrogenase); and
7. blood urea nitrogen (BUN).

The reagents for performing the diagnostic analyses for the above constituents react similarly, contain some common labile ingredients, and some of the chemical reactions involved are common. The following Reaction Scheme I is presented as a model to illustrate the general nature of the reactions involved:

REACTION SCHEME I

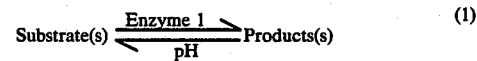

(1)

(2)

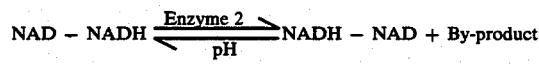

(3)

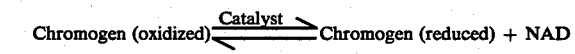

All enzymic reactions listed above will follow this general scheme, where reaction (2) is usually referred to as the coupling reaction, reactions (2) or (3) are the measuring reactions, and reaction (1) may be characterized as the primary reaction. It is understood, however, that not all three reactions are required for measurement, in fact, they may be limited to two, or one. In the case of the ultraviolet measurement of lactic dehydrogenase (LDH) activity, only reaction (2) is involved, as follows:

REACTION SCHEME II—LDH

Conversely, more than the three reactions listed can be involved as in the case of creatine phosphokinase (CPK):

REACTION SCHEME III—CPK

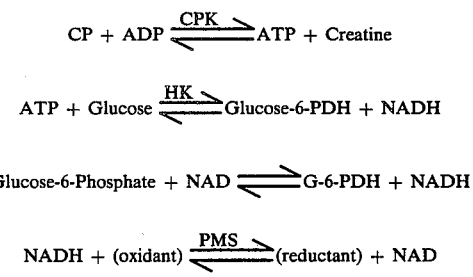

(1)

(2)

(3)

(4)

In this case, reactions (2) and (3) may be considered the coupling reactions, reactions (3) or (4) the measuring reactions, and reaction (1) the primary reaction.

The following symbols are used herein and in the above reaction schemes. The symbols used are the generally acceptable symbols for the clinical diagnostic field.

SYMBOLS

CP = Creatine phosphate
ADP = Adenosine-5'-diphosphate
ATP = Adenosine triphosphate
HK = Hexokinase
NAD = nicotinamide-adenine dinucleotide
NADH = nicotinamide-adenine dinucleotide, reduced
G-6-PDH = Glucose-6-phosphate dehydrogenase
INT = tetrazolium salt
PMS = phenazine methosulfate
L-ASP = L-aspartic acid
OAA = oxalacetic acid
GLU = glutamic acid Referring to the Reaction Scheme I, it becomes obvious and is general knowledge that the use of the reaction sequence permits the analytical quantitation of either the reaction substrates/products or the catalyzing enzymes.

The quantitation of these constituents in biological fluids is a well accepted and widely used diagnostic tool in diagnosis and treatment of human and animal disease states.

SUMMARY OF THE INVENTION

Labile enzymes are treated according to the invention resulting in long term stability without affecting enzymic reactivity or photometric absorptivity. The invention provides reagents where quality control is assured through manufacturing, packaging, storage, and use. The inconvenience of rigid package size is eliminated as is the high cost of packaging, freeze drying, and reagent waste. The liquid stabilized soluble enzyme solutions provide application flexibility. Separation of the ingredients is easily accomplished with negligible manufacturing cost. The liquid stabilized soluble enzyme solutions herein provide the flexibility of triggering the desired enzymic reaction after all side reactions have been dissipated.

The stabilized soluble enzymes of the invention are assessed in studies which compare the enzyme reagents with fresh reagents. The studies show a 1:1 correlation between aged aqueous and fresh reagents with comparable sensitivity and precision.

In diagnostic enzymology, the stabilization of enzyme reagents in a ready-to-use liquid media is a new and exciting approach to satisfy the needs of the clinical laboratory and the reliability demands, of the regulatory authorities. The flexibility of stabilized liquid enzyme systems insures their applicability to automated instrumentation, as well as their convenience in manual testings without reagent waste due to limited shelf life.

Stabilization of labile enzymes in solution is accomplished in accordance with the invention by reacting in a liquid media an enzyme to be stabilized with a polymer having pendant groups capable of covalently bonding with pendant groups on the enzyme. The enzyme and polymer are also mixed with at least one composition which affects the activity of the enzyme. Such composition which can affect the activity of the enzyme can be a substrate for the enzyme, a product produced from an enzymic reaction between the substrate and enzyme, an activator for the enzyme and/or an inhibitor for the enzyme. There can also be added a composition which reacts competitively with the pendant groups of the polymer. That is, a compound can be added which competes with the pendant groups on the enzyme in bonding with the pendant groups on the polymer. For example, protein-like compositions such as albumin and gelatin can be added to compete in reacting with the pendant groups of the polymer.

The polymer having pendant groups capable of covalently bonding with pendant groups on the enzyme can be a polymer having structural units with the formula:

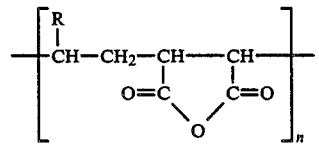

wherein n is an integer and R can be a group selected from hydrogen, alkyl, alkenyl, alkynyl, cycloalkyl, aryl, alkaryl, aralkyl, and

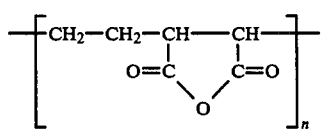

A particularly preferred polymer having such a structure is a copolymer of ethylene and maleic anhydride. The maleic anhydride moiety of the polymer reacts with the pendant amine groups of the enzyme.

Other polymers having utility herein are anhydrides of polyacrylic acid and polymethacrylic acid. Such polymers can be prepared separately or as an intermediate generated in situ. For example, the applicable structures and generation scheme of such polymers is as follows:

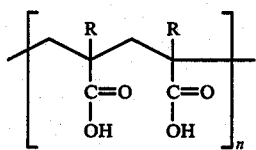

wherein when R is H, the polymer is polyacrylic acid, and wherein when R is CH₃, the polymer is polymethacrylic acid.

Upon application of heat and vacuum to such a polymer or by dehydrating such a polymer with a suitable dehydrating agent, such as dicyclohexyl carbodimide, an intermediate having the following structure is generated in situ:

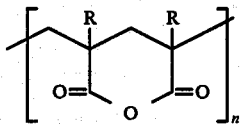

Enzymes which can be stabilized in a solution formed by the method herein include enzymes such as oxidoreductases, transferases, and hydrolases. In addition, the following enzymes, as identified by their number assigned by the International Union of Biochemistry, can be stabilized in solution by the method herein:

| | | |
|---|---|---|
| 1. | Malic dehydrogenase (MDH) | E.C. 1.1.1.37 |
| 2. | Creatine kinase (CK, CPK) | E.C. 2.7.3.2 |
| 3. | Alkaline phosphotase (AP, ALP, ALK-Phos.) | E.C. 3.1.3.1 |
| 4. | Aspartate aminotransferase (AST, OT, GOT,) | E.C. 2.6.1.1 |
| 5. | Alanine aminotransferase (ALT, PT, SGPT) | E.C. 2.6.1.2 |
| 6. | gamma Glutamyl transpeptidase (γGT, γGTP) glutamic oxalacetic transaminase (SGOT) glutamic pyruvic transaminase (GPT) | E.C. 2.3.2.1 |
| 7. | alpha Amylase | E.C. 3.2.1.1 |
| 8. | beta Amylase | E.C. 3.2.1.2 |
| 9. | Lactate dehydrogenase (LD, LDH, (Lactic dehydrogenase) | E.C. 1.1.1.27 |
| 10. | Glucose-6-phosphate dehydrogenase (G6PDH) | E.C. 1.1.1.49 |
| 11. | Hexokinase (HK) | E.C. 2.7.1.1 |
| 12. | Glucose dehydrogenase | E.C. 1.1.1.47 |
| 13. | Glucose oxidase | E.C. 1.1.1.34 |
| 14. | Peroxidase (HRP, HPO, PO) | E.C. 1.11.1.7 |
| 15. | Glycerol dehydrogenase | E.C. 1.1.1.6 |
| 16. | Glutamate dehydrogenase | E.C. 1.4.1.3 |
| 17. | Cholesterol oxidase | E.C. 1.1.3.6 |
| 18. | Cholesterol esterase | E.C. 3.1.1.13 |
| 19. | Lipase | E.C. 3.1.1.3 |
| 20. | Uricase | E.C. 1.7.3.3 |
| 21. | Urease | E.C. 3.5.1.5 |
| 22. | Glycerol kinase | E.C. 2.7.1.30 |

In addition to these enzyme groups, represented by examples herein, enzymes such as lyases, ligases, and isomerases may also be stabilized by the present invention.

The stability of the enzyme in the liquid media is enhanced by mixing with the polymer and enzyme at least one composition which affects the activity of the enzyme, which composition is selected from the group consisting of a substrate for the enzyme, a product of the enzyme and substrate, an activator for the enzyme, and an inhibitor for such enzyme.

The liquid media in which the enzyme is stabilized comprises an aqueous solution of an organic solvent selected from dimethyl sulfoxide, acetone, dimethylformamide, and pyridine. The liquid media can further comprise a buffering agent providing a pH from about 5 to about 10. The buffering agent is selected from the group consisting of tris(hydroxymethyl)aminomethane, imidazole, triethanol amine, and phosphate buffers.

Additional compositions can be added to the enzyme and polymer reaction mixture or solution. Such other compositions include protein-like materials such as protein-like materials selected from albumin and gelatin.

Although the applications of the invention set forth herein relate primarily to the field of clinical biochemistry, it should be obvious to one well versed in the art that the utility of the invention extends to other areas. A wide variety of industrial, pharmaceutical and cosmetic processes and products utilize enzymes in solution, in suspension and immobilized on solid surfaces. The property of enhanced thermal stability of enzymes, such as is conferred by this invention, is widely sought. Enzymes stabilized by the method described herein produce essentially homogeneous aqueous solutions, but are readily separated from reactants and products by a variety of techniques including dialysis and ion exchange. The higher temperatures tolerated by the stabilized enzymes can lead to shorter reaction times in batch and continuous industrial processes. The use of such stabilized enzymes in formulated products can lead to longer product shelf life and/or less stringent storage conditions.

BRIEF DESCRIPTION OF THE DRAWINGS

FIG. 1 is a schematic illustration of an enzyme;

FIG. 2 is a schematic illustration of the enzyme of FIG. 1 showing the enzyme itself blocking its active site;

FIG. 3 is a schematic illustration of a reaction of the enzyme of FIG. 1 with a polymer having reactive pendant groups;

FIG. 4 is a schematic illustration of the enzyme of FIG. 3 illustrating how such polymer can block the active site; and FIG. 5 is a schematic illustration showing how additional compositions can react with the polymer and maintain the active site free to react with a substrate.

DETAILED DESCRIPTION OF THE INVENTION

The stabilized soluble enzymes herein and prepared by the method disclosed herein can be used in the clinical field for the determination of various constituents in biological fluids.

The stabilized soluble enzymes are prepared by reacting in a liquid media an enzyme with a polymer having pendant groups capable of covalently bonding with pendant groups on the enzyme. In addition to reacting such a polymer with the enzyme, there can also be mixed with the enzyme and polymer at least one composition which affects the activity of the enzyme. For example, such a composition can be selected from the group consisting of the substrate for the particular enzyme, the product of the substrate and enzyme reaction, an activator for the enzyme, and an inhibitor for such enzyme. The specific composition selected to be mixed with the enzyme and polymer depends upon the enzyme, as the composition which affects the activity of the enzyme may be specific to the particular enzyme.

In addition to the enzyme and polymer and the composition which affects the activity of the enzyme, there can also be added a composition which can react with the available pendant groups of the polymer. For example, such an additional composition can be a protein-like composition, e.g., albumin, gelatin, and the like.

The enzymes which can be formulated into a stable solution by the method herein include enzymes that are dehydrogenases, transaminases, and peptidases. In particular, specific enzymes which can be stabilized in a soluble form by the method herein include:

1. Malic dehydrogenase (MDH)
2. Creatine kinase (CK, CPK)
3. Alkaline phosphotase (AP, ALP, ALK-Phos.)
4. Aspartate aminotransferase (AST, OT, GOT, SGOT)
5. Alanine aminotransferase (ALT, PT, GPT, SGPT)
6. gamma Glutamyl transpeptidase (γGT, γGTP)
7. alpha Amylase
8. beta Amylase
9. Lactate dehydrogenase (LD, LDH, Lactic dehydrogenase)
10. Glucose-6-phosphate dehydrogenase (G6PDH)
11. Hexokinase (HK)
12. Glucose dehydrogenase
13. Glucose oxidase
14. Peroxidase (HRP, HPO, PO)
15. Glycerol dehydrogenase
16. Glutamate dehydrogenase
17. Cholesterol oxidase
18. Cholesterol esterase
19. Lipase
20. Uricase
21. Urease
22. Glycerol kinase.

Chemically, every enzyme known so far is a protein. Many enzymes are complex proteins having a specific sequence of amino acids. As enzymes are comprised of proteins and thereby amino acids, they can have pendant amine groups. For example, proteins are comprised of amino acids, including lysine and arginine, linked together through peptide linkages and, as such, can provide pendant amine groups. A schematic illustration of an enzyme is illustrated in FIG. 1. In FIG. 1, an enzyme 10 is illustrated as a closed molecular structure of amino acids connected through peptide linkages. The enzyme 10 has an active site 12 which can react with a substrate selected for the enzyme. The ability of an enzyme to attract and react with its substrate relates to the activity of the enzyme.

There are basically three structures to an enzyme. The first structure is that of the linking of amino acids and proteins through various peptide linkages to form the enzyme. The secondary structure of an enzyme is brought about by cross-linking among and between the amino acids of the molecular structure. The tertiary structure of an enzyme is brought about by the orientation of the enzyme in space. That is, the tertiary structure of an enzyme is based upon the configuration that the enzyme molecule occupies with regard to itself and portions of itself. It is believed that denaturization or loss of activity of an enzyme can be brought about by destruction of such tertiary structure of the enzyme. Thus, if the teritary structure of an enzyme can be maintained, the enzyme can be said to have been stabilized. An enzyme can also lose its activity by having some other composition react with the enzyme or bond to the enzyme to effectively block the active site of the enzyme. In addition, a reaction of the composition at some other site on the enzyme can have some effect on the active site. For example, a composition can react at a position on the enzyme to have the effect of closing the enzyme molecule upon itself as depicted in FIG. 2, which effectively blocks the active site. Such an effect is called allosteric inhibition. In addition, another composition can react with the enzyme at a site other than the active site, which other composition can affect or change the electrostatic affinity of the enzyme for its substrate at the active site.

As an enzyme is a three-dimensional chemical composition, and as the activity of the enzyme can depend upon the configuration and orientation of the enzyme (the tertiary structure), the method herein provides a process for stabilizing an enzyme by protecting or maintaining the tertiary structure of the enzyme. The enzyme to be stabilized is reacted with a polymer having pendant groups which can react with the enzyme. For example, the polymer can have pendant groups which can react with pendant amine and/or oxygen present in the enzyme structure. It has been found herein that a polymer having pendant anhydride groups or having anhydride moities along or in the polymer backbone can provide a capability of covalently bonding such pendant anhydride groups with pendant groups on an enzyme.

Polymers which have pendant anhydride groups or polymers having structural units with the formula:

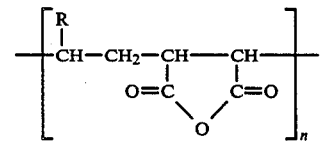

wherein n is an integer and R can be a group selected from hydrogen, alkyl, alkenyl, alkynyl, cycloalkyl, aryl, alkaryl, aralkyl, and

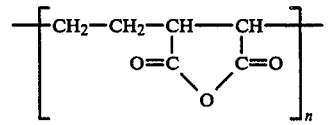

are capable of covalently bonding with protein molecules within the enzyme structure such as through amine groups within the structure.

Other polymers having utility herein are anhydrides of polyacrylic acid and polymethacrylic acid. Such polymers can be prepared separately or as an intermediate generated in situ. For example, the applicable structures of such polymers are as follows:

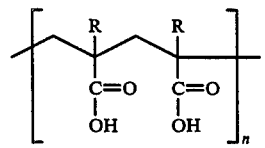

wherein when R is H, the polymer is polyacrylic acid, and wherein when R is CH₃, the polymer is polymethacrylic acid.

Upon application of heat and vacuum to such a polymer or by dehydrating such a polymer with a suitable dehydrating agent, such as dicyclohexyl carbodimide, an intermediate having the following structure is generated in situ:

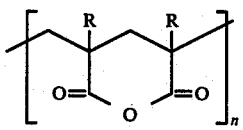

An especially preferred polymer having the above formula is ethylene-maleic anhydride. An ethylene-maleic anhydride copolymer is commercially available from Monsanto Company as a product designed EMA resins. For the purposes of the invention described herein, such commercially available ethylene-maleic anhydride resins are acceptable. The ethylene-maleic-anhydride copolymers are available commercially with average molecular weights of about 8,000, 25,000, and 100,000. In addition, cross-linked ethylene-maleic anhydride copolymers are commercially available and such cross-linked polymers also have utility in the method herein. It was found herein that the higher molecular weight ethylenemaleic anhydride copolymers provided a better stability and greater percentage recovery of activity than the lower molecular weight maleic anhydride polymers. However, the lower molecular weight anhydride polymers can be used in the process herein to provide an acceptable stability and recovery of activity.

It is believed that the ethylene maleic anhydride polymer reacts with pendant amine groups extending from the enzyme structure as is illustrated by the following reaction sequence:

REACTION SEQUENCE

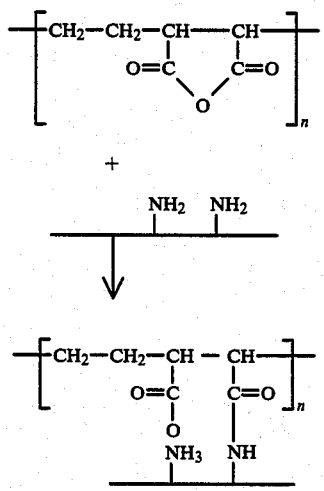

Although it is not fully understood, it is believed that the polymer covalently bonds to the enzyme and holds the enzyme in its active configuration. Although not to be bound by such a theory, the theory of stabilization of soluble enzymes as produced by the method herein is illustrated in FIGS. 3 through 5. With regard to FIG. 3, an enzyme 10 is illustrated having an active site 12. The enzyme is reacted with a polymer 14 having pendant groups capable of covalently bonding to the enzyme. Upon reacting the polymer with the enzyme, covalently bonded linkages 16 are formed between the polymer and enzyme. It has been shown empirically that the resulting reaction product of the enzyme and polymer exhibits a stability greater than a solution of the enzyme without such a polymer. It is believed that the presence of the polymer tends to retain the tertiary structure of the enzyme and thus can maintain the activity of the enzyme.

However, as the polymer can react through its pendant groups with pendant groups from the enzyme, there is a possibility of the polymer reacting with the enzyme at a location whereby the polymer itself either blocks the active site or effectively closes the active site, such as by allosteric inhibition. With regard to FIG. 4, an enzyme 10 is illustrated wherein the polymers 14 have reacted with the enzyme to effectively block the active site and prevent the substrate from reacting with the enzyme. The presence of the polymer as an inhibitor of activity for an enzyme was established by low percentage activity yields when reacting an enzyme with such a polymer. Although enzymes reacted with a polymer alone exhibit a greater stability than enzymes not reacted with such a polymer, the percentage yield of activity of the resultant reacted enzyme over that of the initial activity of the enzyme prior to reaction is generally low. The activity of the enzymes after reaction with the polymer, however, is more stable than the non-reacted enzymes.

Applicants herein found that the soluble enzymes could be stabilized more efficiently and effectively by adding additional compositions to the reaction mixture of the enzyme and polymer. Applicants also found that the order of reaction could be modified to provide a greater percentage yield of activity and/or stability of the resultant stabilized soluble enzyme. Applicants found that such other compositions which can be added to the reaction mixture of the enzyme and polymer include compositions selected from the group consisting of the substrate for the enzyme, the product of the enzyme and substrate, activators for the enzyme, and inhibitors for the enzyme. The specific substrate, product, activator and/or inhibitor added to the reaction mixture depends upon the enzyme to be stabilized. It is believed herein that since the enzymic reaction of the enzyme with the substrate is a reversible reaction to provide the product, the presence of substrate, product, activators and/or inhibitors keeps the active site open and prevents or inhibits the polymer from reacting with the enzyme so as to block or otherwise deleteriously affect the active site.

The selection of the quantity of substrate, product, activators and/or inhibitors to be added to the reaction mixture of the enzyme and polymer depends upon the enzyme and the enzymic reaction of the substrate and polymer. For example, the addition of too much product can change the equilibrium of the enzyme and substrate reaction so as to increase the time for a clinical diagnostic assay to be conducted with the stabilized soluble enzyme solution prepared by the method herein, unless such added product is separated from the stabilized enzyme by, for example, dialysis.

It has also been found that the soluble enzymes can be further stabilized and the activity recovery can be enhanced by adding compositions to the reaction mixture which can also react with the available pendant groups on the polymer. Such other compositions can be any compositions which can react with the pendant groups on the polymer. For example, other protein-like compositions such as albumin, gelatin, and polymers such as dextran can be added to react with the pendant groups of the polymer. The substrate, product, activators and/or inhibitors may also react directly with the pendant groups on the polymers. Of course, whether such compositions react with the polymer depends upon the nature of the substrate, product, activator and/or inhibitor. It is believed that such compositions which can react with the pendant groups on the polymer can help stabilize the enzyme by helping maintain the enzyme in its tertiary structure. In addition, such compositions can react with the polymer to form a matrix-like environment for holding and maintaining the tertiary structure of the enzyme. With regard to FIG. 5, there is disclosed a schematic illustration of such a matrix-like environment. In FIG. 5, an enzyme 10 having an active site 12 is maintained in its tertiary structure by reacting the enzyme with a polymer 14. The polymer 14 covalently bonds to the enzyme through pendant groups forming linkages 16 between the polymer and enzyme. The presence of substrate, product, activators and/or inhibitors can maintain the active site 12 open during the reaction between the enzyme and polymer. Additionally, reactive compositions R, $R_1$, $R_2$ can be added to the reaction mixture to react with the polymer. Such additional reactive compositions can help form the matrix-like environment.

Applicants have found that for some enzymes, it is preferable to react the polymer with such other compositions which can react with the polymer, prior to reacting the polymer with the enzyme. By reacting the polymer with such other compositions first, some of the available active pendant groups on the polymer can be reacted and thereby blocked from reacting with the available pendant groups on the enzyme. By tying up such reactive pendant groups on the polymer prior to reacting with the enzyme, the opportunity of the polymer to react excessively and deleteriously affect the active site of the enzyme may be reduced. With other enzymes, the order of reaction of the various compositions does not substantially affect the stability or percentage recovery of activity of the enzyme.

The enzymes stabilized by the method herein are soluble stabilized enzymes. As the enzymes are in a soluble form, they can be readily used in clinical diagnostic assays. The stabilized soluble enzymes have a relatively long shelf life and retention of activity as compared to state-of-the-art enzymic solutions. The liquid media environment in which the reaction between the enzyme and polymer occurs can be any suitable liquid environment in which the enzyme and polymer are soluble. Preferred liquid environments include aqueous solutions of organic solvents selected from the group consisting of dimethyl sulfoxide, acetone, dimethylformamide, and pyridine. The selection of the specific organic solvent depends upon the enzyme. For example, some enzymes may lose activity when blended with a particular organic solvent, such as, for example, acetone. However, the overall stability and recovery of activity provided by the method herein can overbalance the deleterious effect of a particular organic solvent for a particular enzyme. Of the above organic solvents, the preferred organic solvent is dimethyl sulfoxide when the polymer to be reacted with the enzyme is a copolymer of ethylene and maleic anhydride. The dimethyl sulfoxide provides a good solvent for the enzyme and polymer without substantially deleteriously affecting the activity of the enzyme.

The liquid media can also be buffered with a suitable buffer solution. For example, the liquid media can comprise an aqueous buffering agent providing a pH from about 5 to about 10. The buffering agent can be selected from the group consisting of tris(hydroxymethyl)aminomethane, imidazole, triethanol amine, and phosphate buffers. Of the buffers, it is preferred to utilize a buffer comprising an aqueous solution of tris(hydroxymethyl)-aminomethane. Such a buffer provides acceptable stability for the enzyme without deleteriously affecting the solubility and activity of the enzyme and the solubility of the polymer. The buffer solution is utilized to maintain the pH of the overall reaction mixture and liquid media within a range from about 5 to about 10. A buffer solution is desirable as the pH can fluctuate when the polymer is an anhydride. For example, in an aqueous solution, the anhydride can hydrolyze and thus affect the pH of the solution if not properly buffered.

The method of forming soluble stabilized enzymes is further described in the following examples which are not intended to be limiting, but which describe the method with regard to particular enzymes and enzyme systems.

EXAMPLE I

A stabilized soluble enzyme solution was prepared having utility in a clinical diagnostic assay for aspartate aminotransferase by the following reaction sequence:

The enzyme MDH used in the assay in an unstable enzyme. When in solution, it is stabilized by the method herein as follows.

A first solution was prepared by mixing 0.225 percent by weight gelatin, 0.1 percent by weight sodium azide ($NaN_3$), 500 mg/dl of NADH and 500 mg/dl of NAD in an aqueous buffer solution comprising 1.1 percent by volume tris(hydroxymethyl)aminomethane.

A second solution was prepared by mixing an ethylene maleic anhydride polymer having an average molecular weight of about 100,000 (EMA-31, commercially available from Monsanto Company) with dimethyl sulfoxide (DMSO). The ethylene-maleic anhydride copolymer was added to make a solution having a concentration of such polymer of about 10 mg/ml.

Equal volumes (1 ml each) of the first and second solutions were mixed and allowed to stand for about 2½ minutes. Such a time permitted reaction between the ethylene, and maleic anhydride copolymer and some of the ingredients of the first solution.

A solution of MDH dissolved in a solvent comprising 50% by volume glycerol and 50% by volume water was added to the resultant mixture formed by mixing the first and second solutions. The MDH solution had an activity of about 13,000 IU/ml. After about 10 minutes, substantially all of the coupling between the enzyme and ethylene maleic anhydride was complete.

The resultant solution exhibited an activity for the MDH of about 130–300 IU/ml.

The stability of the resultant solution can also be further improved by adding to it a solution comprising 600 mm of L-ASP and 0.3 percent by weight gelatin in an 0.3% aqueous buffer solution of tris(hydroxymethyl)aminomethane having a pH of about 7.8.

The resultant solution exhibits a greater retention of activity than state-of-the-art solutions of MDH. Generally, such state-of-the-art MDH solutions, when heated to about 41° C. for 2 hours, lose all activity. The MDH solution prepared in accordance with this example exhibits about a 50% retention of reactivity when heated to about 41° C. for up to 93 hours.

EXAMPLE II

The procedure of EXAMPLE I was repeated in every essential detail except that the MDH enzyme solution was reacted with the first solution prior to mixing and reacting the first solution with the second solution of ethylene, and maleic anhydride copolymer in DMSO.

The resultant solution exhibits an activity less than the solution formulated in EXAMPLE I and is about an activity yield of about 5% as compared to the 10–25% yield of the enzyme solution of EXAMPLE I.

EXAMPLE III

The procedure of EXAMPLE I was repeated in every essential detail. The stabilized soluble enzyme was creatine kinase which is generally very labile to heat and other factors.

A first solution was prepared by dissolving 0.225 percent by weight gelatin, 0.1 percent by weight $NaN_3$, 5 percent by weight albumin, 1 weight percent dextran, 1 weight percent ADP, and 0.1 percent by weight mercapto ethanol in an aqueous buffer solution of 1.1 percent by volume tris(hydroxymethyl)aminomethane.

A second solution of EMA-31 in DMSO was prepared as in EXAMPLE I.

The first and second solutions were blended in equal volumes and allowed to stand. Creatine kinase (CK) was then added in an amount of about 5000 IU/ml.

The resultant solution had a gel-like consistency. The activity of the CK in the resultant solution was about 500 IU/ml calculated with regard to the initial activity and when calculated in considering the one to one dilution, the activity is about 250 IU/ml.

It was found that if the mercapto ethanol were removed, the resultant solution did not exhibit as much gel-like consistency.

It was also determined that the sequence of adding the enzyme did not influence the final exhibited activity. For example, the enzyme when added to the first solution prior to mixing the first and second solutions exhibited a stability about the same as described in this example.

The resultant solution exhibits a stability of retention of about 60% of its enzyme activity when heated to about 41° C. for 72 hours. Normally, a solution of CK, if heated to about 41° C., loses substantially all of its enzymic activity within about one hour.

EXAMPLE IV

The procedure of EXAMPLE I was repeated in every essential detail. The enzyme stabilized was serum glutamic oxalacetic transferase (SGOT).

A first solution was prepared by dissolving about 0.225 percent by weight gelatin, one percent by weight L-ASP, one percent by weight α-ketoglutarate (α-Kg) and 5 percent by weight albumin an an aqueous buffer solution of 1.1 percent by volume tris(hydroxymethyl)aminomethane.

A second solution was prepared of ethylene maleic anhydride in DMSO by the procedure in EXAMPLE I.

The first and second solutions were mixed in equal volumes (1 ml each) and the resultant third solution permitted to stand for about 2 minutes.

About 0.1 ml of an SGOT solution having an activity of about 1000 IU/ml was added to the third solution. After about 10 minutes, the resultant enzymic solution exhibited an activity of about 100–150 IU/ml.

This resultant enzymic solution can be diluted with an albumin solution (human serum albumin, bovine serum albumin) or gelatin in a buffer solution providing a pH between about 5 to about 10.

The resultant solution exhibits a retention of about 100% of the enzyme activity when heated to about 41° C. for about 72 hours. Normally, an aqueous solution of the enzyme retains about 50% of its activity when heated to about 41° C. for about 5 hours.

An increase in the yield of activity can be achieved by adding an activator of pyridoxal phosphate to the first solution.

EXAMPLE V

The procedure of EXAMPLE IV was repeated in every essential detail with the exception that the enzyme was aspartate amino transferase (AST).

EXAMPLE VI

The procedure of EXAMPLE IV was repeated in every essential detail with the exceptions that L-alanine was substituted for L-ASP and glutamic pyruvic transaminase (GPT) or (SGPT) was substituted for SGOT.

EXAMPLE VII

The procedure of EXAMPLE IV was repeated in every essential detail except that L-alanine was substituted for L-ASP.

EXAMPLE VIII

The procedure of EXAMPLE I was repeated in every essential detail. The enzyme stabilized in this experiment was lactic dehydrogenase (LDH). Generally, LDH is stable in a 50% glycerol solution if buffered to a pH of about 7.0±2. However, once such an LDH enzymic solution is diluted with a buffered protein-like matrix such as albumin, it loses activity. For example, a normally diluted LDH solution having an activity of about 400 IU/l when heated to about 41° C. for 24 hours exhibits an activity of about 50–100 IU/l.

A first solution is prepared by dissolving 0.225 percent by weight gelatin, 5 percent by weight albumin, and 0.1 percent by weight $NaN_3$ in an aqueous buffered solution comprising 1.1 percent by volume tris(hydroxymethyl)aminomethane.

A second solution of ethylene maleic anhydride in DMSO is prepared as in EXAMPLE I.

The first and second solutions are mixed in a 1:1 volume ratio and allowed to react upon standing for about 2 minutes. About 0.1 ml of a buffered stock solution of LDH having an activity of about 5000 IU/l was added. When the resultant solution is diluted in a buffered protein-like matrix and when such a diluted enzymic solution is heated to about 41° C., it retains substantially all of its activity (approximately 400 IU/l) after 72 hours.

It was also determined that the percent yield of activity would be increased by adding NAD and/or NADH to the first solution.

EXAMPLE IX

The procedure of EXAMPLE VIII was repeated in every essential detail with the exception that the enzyme γ-GTP was substituted for the enzyme LDH.

In a similar stability study, the γ-GTP stabilized enzyme solutions retained substantially all of its activity (approximately 400 IU/l) when heated for 72 hours at about 41° C.

EXAMPLE X

The procedure of EXAMPLE VIII was repeated in every essential detail with the exception that the enzyme ALK-PHOS was substituted for the enzyme LDH.

The resultant enzymic solutions exhibit a similar stability.

However, the addition of NAD and/or NADH to the first solution does not affect the activity to any appreciable extent. It was determined that the addition of the activator magnesium soluble salt of magnesium) increases the percentage yield of enzyme activity and stability.

EXAMPLES 11-24

In all of these examples, the procedure of EXAMPLE I is repeated in every essential detail except that the following enzymes are utilized:

| Ex. No. | Enzyme |
|---|---|
| 11 | amylase |
| 12 | G-6-PDH |
| 13 | hexokinase (HK) |
| 14 | glucose dehydrogenase |
| 15 | glucose oxidase |
| 16 | peroxidase |
| 17 | cholesterol esterase |
| 18 | cholesterol oxidase |
| 19 | glycerol dehydrogenase |
| 20 | lipase |
| 21 | uricase |
| 22 | urease |
| 23 | glutamate dehydrogenase |
| 24 | glycerol kinase |

What is claimed is:

1. A method for forming a soluble stabilized enzyme solution comprising the steps of:
    (a) forming a first solution by mixing up to about 0.225 percent by weight gelatin, up to about 0.1 percent by weight NaN$_3$, up to about 500 mg/dl nicotinamide-adenine dinucleotide, reduced (NADH), and about 500 mg/dl nicotinamide-adenine dinucleotide (NAD) in water with about 1.1 percent by weight tris(hydroxymethyl)aminomethane;
    (b) forming a second solution by dissolving a copolymer of ethylene and maleic anhydride in a concentration of about 10 mg of the ethylene-maleic anhydride copolymer per milliliter of dimethyl sulfoxide;
    (c) mixing the first and second solutions to form a third solution; and
    (d) adding a fourth solution of maleic dehydrogenase (MDH) dissolved in a solvent comprising 50 percent by volume glycerol and 50 percent by volume water to the third solution and reacting pendant groups of maleic dehydrogenase with the pendant groups of the copolymer of ethylene and maleic anhydride to form a solubilized stable solution of maleic dehydrogenase.

2. A method as recited in claim 1 further comprising the step of adding to the solubilized stable enzyme solution a fifth solution comprising 600 mM L-aspartic acid (L-ASP) and 0.3 percent by weight gelatin dissolved in an aqueous buffer solution of tris(hydroxymethyl)aminomethane having a pH of about 7.8.

3. A method for forming a soluble stabilized enzyme solution comprising the steps of:
    (a) forming a first solution by mixing up to about 0.225 percent by weight gelatin, up to about 0.1 percent by weight NaN$_3$, up to about 500 mg/dl nicotinamide-adenine dinucleotide, reduced (NADH), and about 500 mg/dl nicotinamide-adenine dinucleotide (NAD) in water with about 1.1 percent by weight tris(hydroxymethyl)aminomethane;
    (b) adding to the first solution a solution of maleic dehydrogenase (MDH) dissolved in a solvent comprising 50 percent by volume glycerol and 50 percent by volume water to form a second solution;
    (c) forming a third solution by dissolving a copolymer of ethylene and maleic anhydride in a concentration of about 10 mg of ethylene-maleic anhydride copolymer per milliliter of dimethyl sulfoxide;
    (d) mixing the second and third solutions to form a fourth solution; and
    (e) covalently reacting in the fourth solution pendant groups of maleic dehydrogenase with pendant anhydride groups of the copolymer of ethylene and maleic anhydride to form a solubilized stable solution of maleic dehydrogenase.

4. A stabilized soluble enzyme solution prepared by the method of claims 2, or 3.

5. A method for forming a soluble stabilized enzyme solution comprising the steps of:
    (a) forming a first solution comprising up to about 0.225 percent by weight gelatin, 0.1 percent by weight NaN$_3$, at least about 5 weight percent albumin, at least about 1 weight percent dextran, at least about 1 weight percent adenosine-5'-diphosphate (ADP), and at least about 0.1 percent by weight mercapto ethanol in an aqueous solution comprising about 1.1 percent by volume tris(hydroxymethyl)-aminomethane;
    (b) forming a second solution comprising a copolymer of ethylene and maleic anhydride dissolved in dimethyl sulfoxide at a concentration of about 10 mg/ml;
    (c) mixing the first and second solutions; and
    (d) adding creatine kinase to the mixture of the first and second solutions and reacting pendant groups of creatine kinase with anhydride groups of the copolymer of ethylene and maleic anhydride to form a soluble stabilized solution of creatine kinase.

6. A method as recited in claim 5 wherein the creatine kinase is added to the first solution prior to mixing the first and second solutions.

7. A stabilized soluble enzyme solution prepared by the method of claims 5 or 6.

8. A method for forming a stabilized soluble enzyme solution comprising the steps of:
(a) forming a first solution by dissolving up to about 0.225 percent by weight gelatin, 1 gram percent L-aspartic acid (L-ASP), 1 percent by weight α-ketoglutarate, and 5 percent by weight albumin in a buffered aqueous solution comprising 1.1 percent by volume tris(hydroxymethyl)aminomethane;
(b) forming a second solution by dissolving a copolymer of ethylene and maleic anhydride in dimethyl sulfoxide in a concentration of 10 mg/ml;
(c) mixing the first and second solutions to form a third solution; and
(d) adding an enzyme selected from the group consisting of aspartate aminotransferase (AST) and glutamic-oxalacetic transaminase (SGOT) to the third solution and reacting pendant groups of the enzyme with anhydride groups of the copolymer of ehtylene and maleic anhydride to form a stabilized soluble enzyme solution.

9. A method as recited in claim 8 wherein the enzyme is added to the first solution prior to mixing the first and second solutions.

10. A method as recited in claim 8 further comprising adding pyridoxal phosphate to the first solution.

11. A stabilized soluble enzyme solution prepared by the method of claims 8, 9, or 10.

12. A method for forming a stabilized soluble enzyme solution comprising the steps of:
(a) forming a first solution by dissolving up to about 0.225 percent by weight gelatin, 1 gram percent L-alanine, 1 percent by weight α-ketoglutarate, and 5 percent by weight albumin in a buffered aqueous solution comprising 1.1 percent by volume tris(hydroxymethyl)aminomethane;
(b) forming a second solution by dissolving a copolymer of ethylene and maleic anhydride in dimethyl sulfoxide in a concentration of 10 mg/ml;
(c) mixing the first and second solutions to form a third solution; and
(d) adding an enzyme selected from the group consisting of aspartate aminotransferase (AST) and glutamic-oxalacetic transaminase (SGOT) to the third solution and reacting pendant groups of the enzyme with anhydride groups of the copolymer of ethylene and maleic anhydride to form a stabilized soluble enzyme solution.

13. A method for forming a stabilized soluble enzyme solution comprising the steps of:
(a) forming a first solution by dissolving up to about 0.225 percent by weight gelatin, 1 gram percent L-alanine, 1 percent by weight α-ketoglutarate, and 5 percent by weight albumin in a buffered aqueous solution comprising 1.1 percent by volume tris(hydroxymethyl)aminomethane;
(b) forming a second solution by dissolving a copolymer of ethylene and maleic anhydride in dimethyl sulfoxide in a concentration of 10 mg/ml;
(c) mixing the first and second solutions to form a third solution which contains an enzyme selected from glutamic pyruvic transaminase (GPT) and alanine aminotransferase (SGPT); and
(d) covalently reacting pendant groups of the enzyme with pendant anhydride groups of the copolymer of ethylene and maleic anhydride in the third solution to form a stabilized soluble enzyme solution.

14. A method as recited in claim 13 wherein the enzyme is added to the first solution prior to mixing the first and second solutions.

15. A stabilized soluble enzyme solution prepared by the method of claims 12, 13, or 14.

16. A method for preparing a stabilized soluble enzyme solution comprising the steps of:
(a) forming a first solution of up to about 0.225 percent by weight gelatin, up to about 5 percent by weight albumin, and about 0.1 percent by weight NaN$_3$ in an aqueous buffer solution comprising about 1.1 percent by volume tris(hydroxymethyl)aminomethane;
(b) forming a second solution by dissolving a copolymer of ethylene and maleic anhydride in dimethyl sulfoxide at a concentration of about 10 mg/ml;
(c) mixing the first and second solutions to form a third solution which contains an enzyme selected from the group consisting of lactate dehydrogenase (LDH), gamma-glutamyl transpeptidase (γ-GTP), and alkaline phosphotase (ALK-PHOS); and
(d) covalently reacting pendant groups of the enzyme with pendant anhydride groups of the copolymer of ethylene and maleic anhydride in the third solution to form a stabilized soluble enzyme solution.

17. A method as recited in claim 16 further comprising adding at least one compound selected from the group consisting of nicotinamide-adenine dinucleotide (NAD) and nicotinamide-adenine dinucleotide, reduced (NADH) to the first solution.

18. A method as recited in claim 16 wherein the enzyme comprises alkaline phosphotase (ALK-PHOS) and a soluble magnesium salt is added to the first solution.

19. A method as recited in claim 16 wherein the enzyme is added to the first solution prior to mixing the first and second solutions.

20. A stabilized soluble enzyme solution prepared by the method of claims 16, 17, 18, or 19.

21. A method for preparing a soluble stable enzyme with enzymatic functionality which comprises reacting, in a liquid medium, pendant groups of an enzyme selected from the group consisting of maleic dehydrogenase, creatine kinase, alkaline phosphotase, aspartate aminotransferase, alanine aminotransferase, gamma glutamyl transpeptidase, alpha amylase, beta amylase, lactate dehydrogenase, glucose-6-phosphate dehydrogenase, hexokinase, glucose dehydrogenase, glucose oxidase, peroxidase, glycerol dehydrogenase, glutamate dehydrogenase, cholesterol oxidase, cholesterol esterase, lipase, uricase, urease, and glycerol kinase with pendant groups of a polymer selected from the group consisting of polyacrylic acid, polymethacrylic acid, a polymer having pendant structural units of the formula:

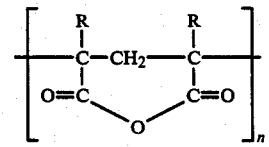

wherein R is a group selected from hydrogen and methyl, and a polymer having pendant structural units of the formula:

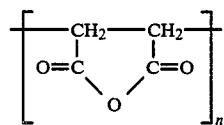
wherein n is an integer, to form covalent bonds between the pendant groups of said enzyme and pendant groups of said polymer, said reaction occurring in the presence of at least one composition which affects the activity of the enzyme, said composition selected from the group consisting of substrate, product, activator and inhibitor for such enzyme.
* * * * *